United States Patent [19]

Holtkamp, Sr.

[11] Patent Number: Plant 6,524

[45] Date of Patent: Jan. 10, 1989

[54] AFRICAN VIOLET PLANT NAMED TRINIDAD

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 55,876

[22] Filed: Jun. 1, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

An African violet plant named Trinidad, characterized by its light lavender flowers with purple on the edge of the two smaller petals, white lightly frilled edges on the other petals; first flash of flowers forming a tight bouquet above the leaves; strong upright flower stems curving toward the center; profuse flowering; vigorous growth habit; medium green, slightly hairy, oval leaves; and long lasting and non-dropping flowering habit.

1 Drawing Sheet

The present invention comprises a new and distinct cultivar of African violet plant, botanically known as *Saintpaulia ionantha,* and hereinafter referred to by the cultivar name Trinidad.

The new cultivar was referred to during the selection process by the designation MH 77/9 and is a mutation of the unpatented cultivar Barbados. Trinidad was discovered growing among a crop of plants of the parent cultivar in commercial greenhouses at Haffen, Federal Republic of Germany. Trinidad was recognized immediately by its light lavender flower color and white, lightly frilled petal margins, with the two smaller petals having darker purple areas approaching the margins. The parent cultivar Barbados was developed in a breeding program in which the female, or seed parent, was a cultivar designated D 198/5 (blue single), and the male, or pollen parent, was a cultivar designated GG 18 (light blue star).

Asexual reproduction of Trinidad by leaf cuttings, as performed by me at Haffen, Federal Republic of Germany, has demonstrated that the combination of characteristics as herein disclosed for the new cultivar are firmly fixed and retained through successive generations of asexual reproduction.

Trinidad has not been observed under all possible environmental conditions. The phenotype may vary significantly with variations in environment such as temperature, light intensity and day length. The following observations, measurements and values describe the new cultivar as grown in a 10 cm pot in Haffen, Federal Republic of Germany and Nashville, Tenn. under greenhouse conditions which closely approximate those generally used in commercial practice.

The following traits have been repeatedly observed and are determined to be basic characteristics of Trinidad which in combination distinguish this African violet as a new and distinct cultivar:

1. Light lavender flowers with white lightly frilled edges, the two smaller petals having a darker purple color toward the edges.
2. First flash of flowers forms a tight bouquet above the leaves.
3. Long-lasting, non-dropping flowers.

4. Each plant carries up to 10 and more upright flower stems, each of which carries 7–10 flowers and more.
5. Profuse flowering.
6. Seed capsule pushes slightly through.
7. Vigorous grower.
8. Plant saleable 9–10 weeks after potting.
9. Medium green, oval leaves, slightly hairy.
10. After maturity, the flowers dry off and remain on the peduncle without becoming infected by botrytis.
11. The flower head builds in three visible incremental steps that flower 14 days apart.
12. Strong upright flower stems curving toward the center.

The new cultivar Trinidad is most similar to its parent Barbados, and is distinguished from Barbados only by flower color.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 2:00 p.m. in Nashville, Tenn. Under cooler growing conditions and more intensive lighting, the light purple color becomes more intense.

Botanical classification: *Saintpaulia ionantha,* Ramat., cv. Trinidad.

Propagation: The new cultivar holds its distinguishing characteristics through successive propagations by leaf cuttings and by division of shoots.

Plant: From 7 to 10 cm tall when grown in pots, and approximately 22–26 cm in diameter when fully grown. The growth rate is vigorous.

*Leaves.*—Shape: Oval. Diameter: 65–70 mm wide and 85–95 mm long. Texture: Leatherlike. Aspect: Velvet, slightly hairy. Ribs and Veins: Underside well pronounced, light green and shiny, purple in between the veins. Color (upper side): Green 136 between A and B. Color (under side):

Red purple in between the greenish veins. Petioles: Strong, upright, brownish purple, hairy.

*Flowers.*—Buds: Bell-shaped, 8–10 mm before opening. Sepals: Five (5) in number, spear-shaped, hairy, dark brown. Calyx: Funnel-shaped. Aspect: Spear-shaped, hairy. Peduncle: Strong, upright, brownish, hairy.

*Individual flowers.*—Size: 35–40 mm. Shape: Single violet-shaped, slightly frilled. Color (upper side): Violet blue 92B with narrow white edges (not visible in photograph); smaller two petals have tinge of darker purple 93C toward edges. Color (under side): Violet blue 91B. Borne: Each flower stem carries 7–12 flowers and more on strong, upright, wire-like peduncles that are free standing above the leaves. Flowering habit: Flowers 8–9 weeks after potting. Corolla: Slightly open flower head, free standing above the leaves.

*Reproductive organs.*—Stamens: Two (2) in number. Anthers: Two with 4 anther cells. Filaments: 5 mm, yellowish green with purple on the edges. Pollen Color: Yellow 7A. Styles: 6 mm, dark purple.

*Roots.*—Normally developed, white when young, turning slightly brownish when older.

Disease resistance: Good.

General observations: Trinidad is a vigorous grower, with attractive velvet medium green leaves. Out of the center, 10 and more strong flower stems appear that are slightly bending toward the center, carrying 7–10 and more single, light lavender flowers with slightly frilled white margins. The 2 smaller petals are purple towards the white edges. Occasionally, an additional very small petal develops. The fully developed flower head has a tight bouquet. Approximately 8–9 weeks after potting the plant is saleable. The flowers are long-lasting and non-dropping and the seed capsule pushes slightly through.

I claim:

1. A new and distinct cultivar of African violet plant named Trinidad, as described and illustrated, and particularly characterized by its light lavender flowers with purple on the edge of the two-smaller petals, white lightly frilled edges on the other petals; first flash of flowers forming a tight bouquet above the leaves; strong upright flower stems curving toward the center; profuse flowering; vigorous growth habit; medium green, slightly hairy, oval leaves; and long lasting and non-dropping flowering habit.

* * * * *

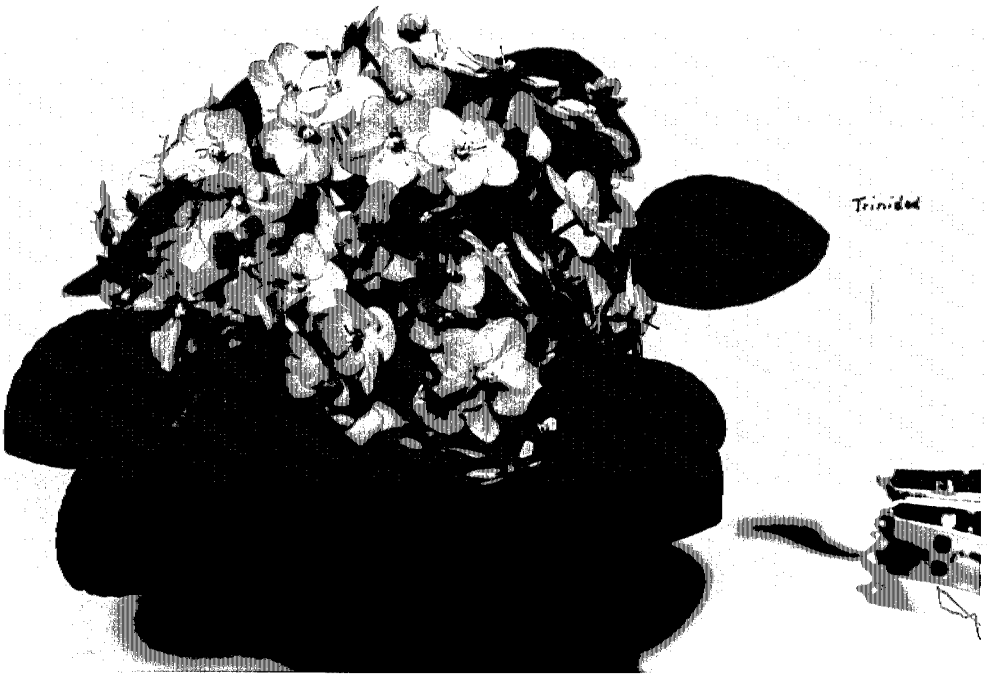
Trinidad